United States Patent [19]

Cusato et al.

[11] 4,229,166
[45] Oct. 21, 1980

[54] PARALLELING TOOL OR GAUGE FOR GENERAL DENTISTRY

[75] Inventors: Anthony J. Cusato, Closter, NJ; Jerome J. Goodman, 25 Pinehill Rd., Closter, N.J. 07624

[73] Assignee: Jerome J. Goodman, Closter, N.J.

[21] Appl. No.: 50,302

[22] Filed: Jun. 20, 1979

[51] Int. Cl.³ .............................................. A61C 19/04
[52] U.S. Cl. ....................................................... 433/72
[58] Field of Search ................ 433/3, 69, 72, 71, 157; 33/174 D, 189, 149 R, 149 E, 150

[56] References Cited

U.S. PATENT DOCUMENTS

| 380,360 | 3/1888 | Spencer | 33/150 |
|---|---|---|---|
| 1,125,576 | 1/1915 | Maier | 433/72 |
| 1,216,596 | 2/1917 | Nishi | 33/174 D |
| 3,879,849 | 4/1975 | Schwartz | 433/3 |
| 3,906,634 | 9/1975 | Aspel | 433/3 |

FOREIGN PATENT DOCUMENTS 850896 12/1939 France ........................ 433/72

*Primary Examiner*—Robert Peshock
*Attorney, Agent, or Firm*—Ralph R. Roberts

[57] ABSTRACT

There is shown a simple paralleling tool or gauge which provides means for the dentist to examine and compare a spacing or arrangement of a patient's teeth with the desired spacing or offset as determined by the dentist and/or assistant. The tool has two blade members which are movable longitudinally with regard to each other along a rivet retainer. End members at right angles to the blade members are pivotally retained at the ends of the blade members. These end members are swung to the desired position to provide the gauge and/or reading and record.

8 Claims, 3 Drawing Figures

PARALLELING TOOL OR GAUGE FOR GENERAL DENTISTRY

BACKGROUND OF THE INVENTION

1. Field of the Invention

With reference to the classification of art as established in and by the United States Patent Office the present invention is believed to be found in the Class entitled "Dentistry" (Class 32) and in particular to the subclass entitled "Instruments" (subclass 40R).

2. Description of the Prior Art

The disclosed paralleling tool for measuring the spacing and offset of teeth provides means for the dentist to measure and precisely establish the desired spacing and offset between teeth. A careful pre-ex search disclosed several patents showing dental appliance systems but these do not show the simple tool provided in the present invention. Among the patents found and presumed pertinent to this invention are U.S. Pat. Nos. 3,879,849 as issued to SCHWARTZ et al as issued on Apr. 29, 1975; 3,986,264 as issued to FAIRSTEIN et al on Oct. 19, 1976; 3,906,634 as issued to ASPEL on Sept. 23, 1975; 4,047,303 as issued to ZIOFSKY et al. as issued on Sept. 13, 1977, and 4,136,449 as issued to PENROD et al as issued on Jan. 30, 1979.

In these and other concepts the apparatus is complex and/or incomplete in the providing of a measuring and recording appliance by which the dentist may measure and record the position of the teeth. Measuring systems using pointer appliances are known but they require the dentist to compute the changes to the tooth alignment or proposed placement. A flexible guide for artificial teeth is shown in the ZIOFSKY patent but insofar as is known the simple tool or appliance as disclosed is not shown or known.

This invention provides a simple, easily-manipible tool that provides a means for recording and measuring tooth spacing, offset and/or positioning of the teeth. The dentist and/or his or her assistant, by using the instrument as to be more fully described, may easily and accurately measure and record the desired information. This instrument is preferably made of sheet stainless steel and is easily cleaned and sterilized.

SUMMARY OF THE INVENTION

This invention may be summarized at least in part with reference to its objects. It is an object of this invention to provide, and it does provide, a prosthetic tool for measuring the offset, spacing change of upper and/or lower teeth of a patient.

It is a further object of this invention to provide, and it does provide, a pivoted blade member tool in which one of the ends of the blade members are further provided with pivoted, short-length, right angle portions. These pivoted ends are disposed on like or mating ends of the two blade members. At least one of the blade members is formed with a lengthwise slot and in this slot is mounted a pivoted retaining member which engages and retains the other blade member to the first blade member. The slot permits the slotted blade member to be moved along this slot and with the mating retained member blade to be pivoted and moved to a desired angle and position. The right-angled end members are now moved to the desired attitude and position.

In brief, the appliance to be hereinafter more fully described includes longitudinal leaf or blade members of similar extents and configuration. One end of these blade or leaf members is bent at more-or-less right angles to provide manipulative grasping means. The other end of these blade members has a tapered and rounded end which includes a small hole or aperture. Short right-angled end members are pivotally attached as by rivets to these ends at small holes formed therein. These short end members are mounted so as to be in like planes and attitudes. The two blade members are secured to each other at their midlengths by a rivet and washer. In one embodiment a mounting hole is provided at one midlength of a blade member and the other end member has the rivet passing through the slot. Preferably the blade members have their manipulative ends bent. These members are preferably of stainless steel sheet metal. Such a material is not subject to a rust problem or appearance and also the several members lend themselves to die cutting and forming for high speed, low cost production.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen a specific embodiment of the paralleling tool or gauge as adopted for use in measuring the spacing and offset of teeth and showing a preferred means for construction and assembly. This specific embodiment has been chosen for the purpose of illustration and description as shown in the accompanying drawing wherein:

BRIEF DESCRIPTION OF THE DRAWING

In the following description and in the claims various details are identified by specific names for convenience. These names are intended to be generic in their application. Corresponding reference characters refer to like members in the two figures of the drawing.

Figure 1:
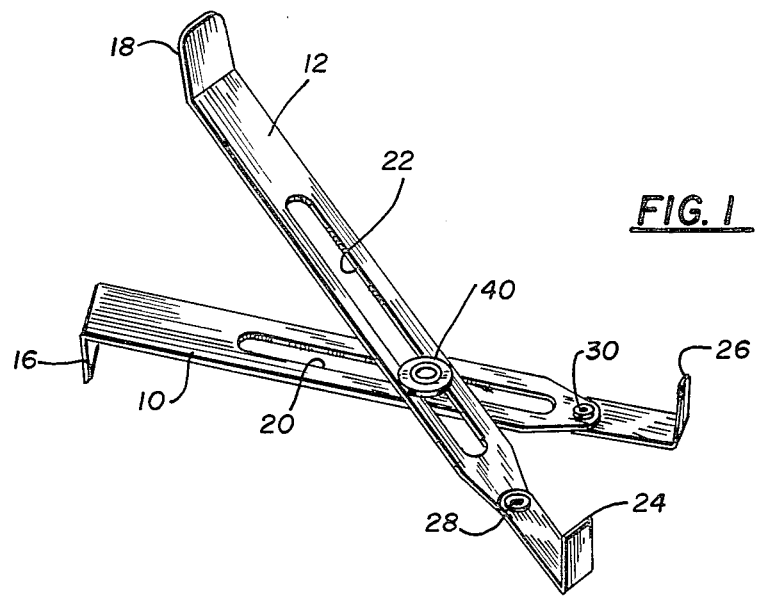
FIG. 1 represents an isometric view of an assembled paralleling tool or gauge of this invention and showing the tool in an assembled condition and ready for adjustment and use.

The drawing accompanying and forming part of this specification discloses details of construction for the purpose of explanation but structural details may be modified without departure from the concept and principles of the invention and the invention may be incorporated in other structural forms than shown.

DESCRIPTION OF THE PREFERRED EMBODIMENT

Referring now to the drawing and in particular to the isometric view of the assembled tool as seen in FIG. 1, the assembled apparatus includes a generally arranged scissor blade or leaf members 10 and 12. As shown these are like members with manipulative bend ends 16 and 18. A longitudinal slot 20 or 22 of like extent and configuration is disposed midlength of the blade or leaf member 10 or 12. The right end of the blade members 10 and 12 have secured thereto in a pivoted arrangement bent end members 24 and 26. A rivet and securing washer 28 and 30 are used to hold the end 24 and the end 26 to the appropriate blade member 10 or member 12. A rivet 32, a washer 34, a spacing washer 36, a washer 38 and securing ferrule 40 are shown as a means of holding the two blade members to each other in pivoted array.

Use and Operation of Tool

For the use of the device it is assumed that the tool is assembled as shown. The pivoted rivet 32 and the retaining ferrule 40 secure the blades 10 and 12 so that these members where and when moved are retained in their adjusted condition and position. The longitudinal slots 20 and 22 enable the blades to be moved to bring one of these members ahead or behind the other. The manipulative bent ends 16 and 18 are used to enable the blade members to be swung and longitudinally positioned as desired. The bend ends 24 and 26 are retained by rivet 28 in a pivoted relationship which is sufficiently tight so that the moved bent ends 24 and 26 are retained in their adjusted and moved condition and position. The blades 10 and 12 and the bent end 24 and 26 are moved to the desired conditions as desired by the dentist or attendant.

Figure 2:
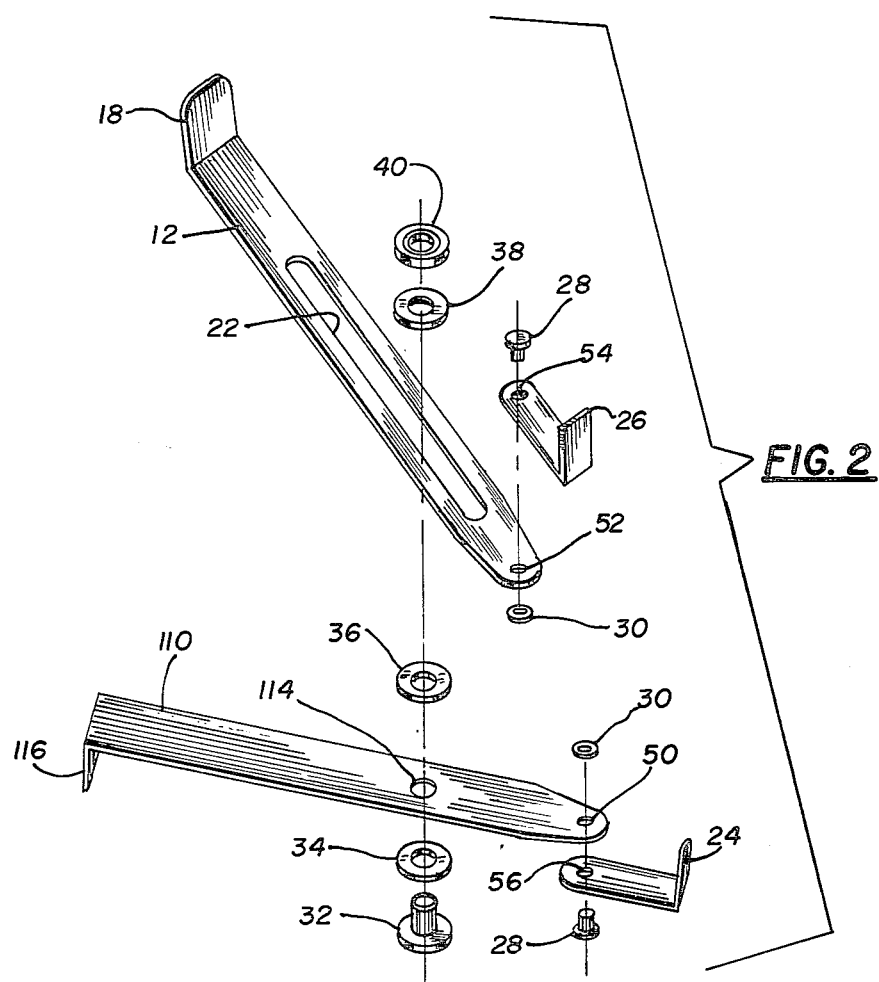
FIG. 2 represents an exploded isometric view of an alternate embodiment of a paralleling tool or gauge, and showing one of the longitudinal blade or leaf members with a rivet hole rather than a slot in its longitudinal extent.

Alternate Construction as seen in FIG. 2

Referring next and finally to the exploded isometric view of FIG. 2 there is depicted a tool much like that of FIG. 1 but with the lower blade member identified as 110. This member does not have a longitudinal slot. A pivot hole or aperture 114 is formed at the midlength of member 110. This hole is sized to be a slide fit for the rivet 32. The end 116 is bent more-or-less at right angles to the main body of the member 110 to provide manipulative means as in the member 10 of FIG. 1. It is to be noted that in the exploded view that holes 50 in member 110 and 52 in member 12 are sized to receive and retain the rivet 28. Holes 54 and 56 are formed in the bent members 26 and 24 to also retain rivet 28.

Use and Operation of the Tool of FIG. 2

It is to be noted that the tool of FIG. 2 is much like that of FIG. 1 as described above. The lower blade member 110 rather than having a longitudinal slot has a hole 114 to receive and retain the pivot rivet 32. The slot 22 in the upper member 12 slides along the rivet 32. The pivoted end members 24 and 26 are retained by the rivets 28 and ferrules 30 when desired or required. In operation this tool is manipulated as in the tool of FIG. 1.

It is to be noted that the blade members 10 and 12 may be made from castings or other metals or of high strength plastics such as ABS (Acrylonitrile-Butadiene-Styrene) or LEXAN (Trademark of General Electric Corporation, Polyamide resin). The turned ends for manipulative purposes are conventionally provided by a turning or bending of the end portions. Other manipulative handle means of course can be provided. This would include added and/or molded means such as handle ends such as is provided with scissors. Washers 34, 36, 38 and ferrule retainer 30 may be altered or eliminated if desired. It is only necessary that the blade members remain in their adjusted position during the period of time that is necessary for measurement and/or positioning by the attendant and/or dentist.

It is to be further noted that the tool above described in detail is moved to bring the blade members into the desired alignment where and when the short bent ends are turned to give the desired parallel measurement. The pivoted end members are preferably of sheet metal but of course may be cast or from extrusions. The tool is adapted to provide only parallel readings of the teeth spacing and offset. As above noted, the manipulation is easy and the sterilization may be achieved without rust problems.

Terms such as "left", "right", "up", "down", "bottom", "top", "front", "back", "in", "out", "clockwise" and the like are applicable to the embodiments shown and described in conjunction with the drawing. These terms are merely for the purposes of description and do not necessarily apply to the position in which the paralleling tool or gauge may be constructed or used.

While a particular embodiment of this tool and alternate embodiment have been shown and described it is to be understood the invention is not limited thereto since modifications may be made within the scope of the accompanying claims and protection is sought to the broadest extent the prior art allows.

What is claimed is:

1. A paralleling tool and gauge for dentists and the like, and providing means for manipulating to a desired position and condition to indicate the desired spacing and offset of teeth, said tool including: (a) a pair of blade members arranged in a scissors relationship with at least one of said blades having a longitudinal slot in and through its midlength; (b) a pivot means holding the two blade members in a near contiguous relationship and with this pivot means extending through the slot and enabling longitudinal movement of one blade with the other, this pivot means retaining the blades so as to be moved only against a determined friction and to the selected attitude and position; (c) a movable end member disposed at one of the ends of each blade, each end member having a support surface by which is placed in a contiguous relationship to a selected end surface of the blade and with the end member having a face surface substantially normal to the mounting surface; (d) a pivot means by and with which each end movable member is pivotally secured to the blade member with said pivot means having a determined friction so that the end member may be selectively moved against said friction to a desired position and condition in which the end members are bent and substantially at right angles and the pivot securing means is a rivet extending through holes in the blade member and end member and securing the movable end member so that the upstanding faces of each of the members are in or may be moved to a common plane; and (e) manipulative on the blades are bent ends formed on each blade so that an attendant may move the several components of the assembled tool to the desired condition.

2. A paralleling tool as in claim 1 in which the tool is made of stainless steel.

3. A paralleling tool as in claim 2 in which the tool is made of stainless steel sheet metal.

4. A paralleling tool as in claim 1 in which the pivot means for securing the two blade members together includes a rivet and a retaining ferrule.

5. A paralleling tool as in claim 1 in which the pivot means for securing the two blade members together includes a rivet and a retaining ferrule.

6. A paralleling tool as in claim 1 in which the blade members at least are made of high strength and temperature resistant plastic such as ABS, LEXAN and the like.

7. A paralleling tool as in claim 6 in which all parts are made of plastic.

8. A paralleling tool as in claim 1 in which only one of the blades has a longitudinal slot and the other blade has a rivet retaining hole formed midway of its length, this hole disposed and sized to retain a through rivet which provides said pivot means.

* * * * *